United States Patent
Fischer et al.

(10) Patent No.: US 8,414,882 B2
(45) Date of Patent: Apr. 9, 2013

(54) LEISHMANIA CHALLENGE MODEL

(75) Inventors: Laurent Bernard Fischer, Sainte Foy les Lyon (FR); Shaden Kamahwi, Rockville, MD (US); Jesus Valenzuela, Gaithersburg, MD (US); Hamide Aslan Suau, Diyarbakir (TR)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 13/296,675

(22) Filed: Nov. 15, 2011

(65) Prior Publication Data
US 2012/0164179 A1 Jun. 28, 2012

Related U.S. Application Data

(60) Provisional application No. 61/415,212, filed on Nov. 18, 2010.

(51) Int. Cl.
*A01N 63/00* (2006.01)
(52) U.S. Cl.
USPC ........................................................ 424/93.1
(58) Field of Classification Search ........................ None
See application file for complete search history.

(56) References Cited

PUBLICATIONS

Collin et al (PLOS Pathogens vol. 5, Issue 5, pp. 1-11, May 2009).*
Melby et al., J. Immunol. 2001;166;1912-1920.
Lawyer et al., Transactions of the Royal Society of Tropical Medicine and Hygiene. (1990) 84, 229-232.
Probst et al., Medical and Veterinary Entomology (2001) 15, 12-21.
Dondji et al., Infection and Immunity, Aug. 2005, p. 5286-5289.
Wilson et al., Microbial Pathogenesis 38 (2005) 147-160.
Kamhawi et al., Science 290, 1351 (2000).
Morris et al., J. Immunol. 2001;167;5226-5230.
Gomes et al., PNAS, Jun. 3, 2008_vol. 105_No. 22_7845-7850.
Kimblin et al., PNAS, Jul. 22, 2008_vol. 105_No. 29_10125-10130.

* cited by examiner

*Primary Examiner* — Albert Navarro
(74) *Attorney, Agent, or Firm* — Judy Jarecki-Black; Chad Kitchen; Merial Limited

(57) ABSTRACT

The present invention provides a method for effectively and reproducibly infecting canines with *Leishmania infantum* using sand flies to vector the parasite. The inventive method comprises several steps, including ensuring canines are naïve to *Leishmania*, infecting the canines using bites of *Leishmania*-infected sand fly bites, and evaluating successful transmission of the *Leishmania* parasites.

8 Claims, 19 Drawing Sheets

FIG. 3
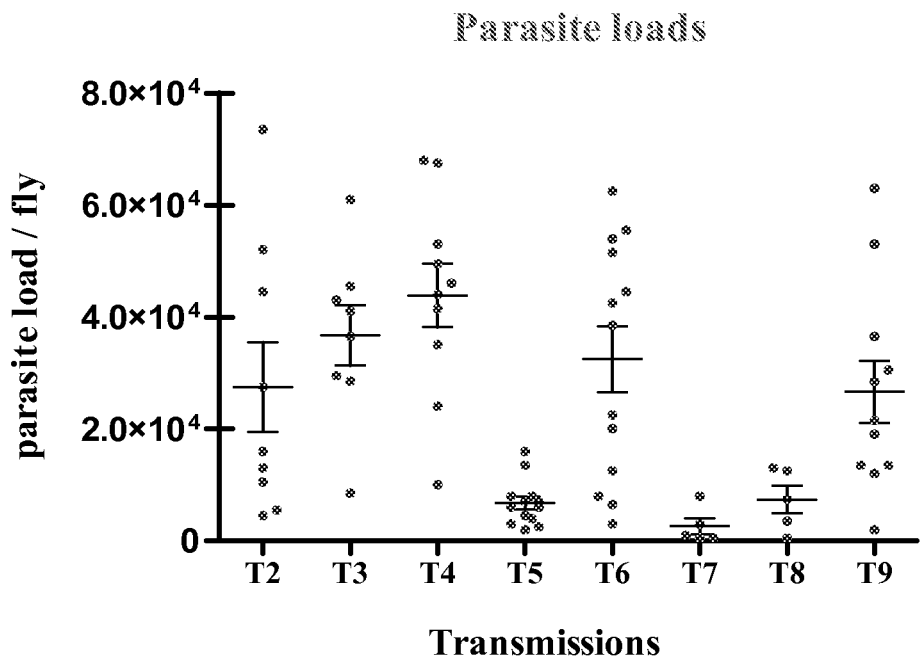
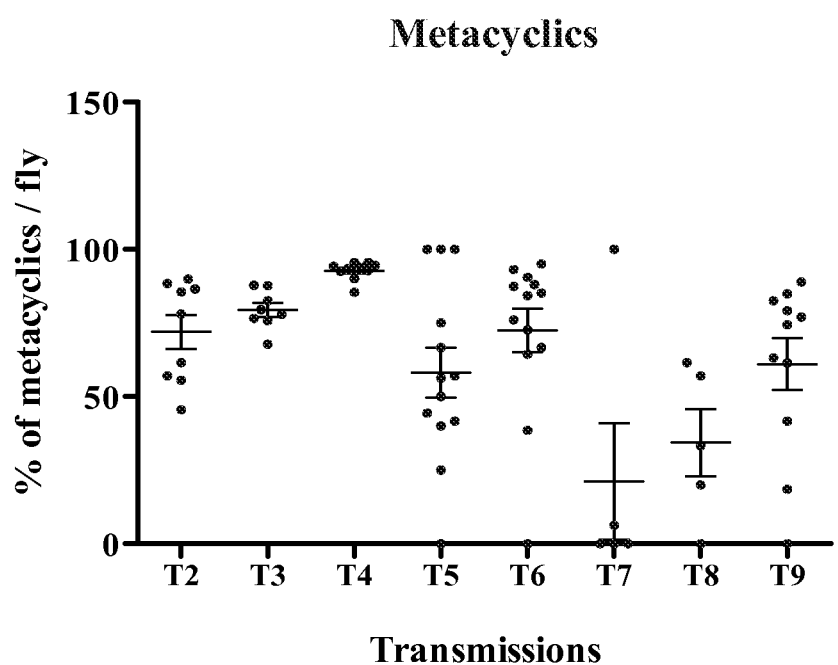

FIG. 4
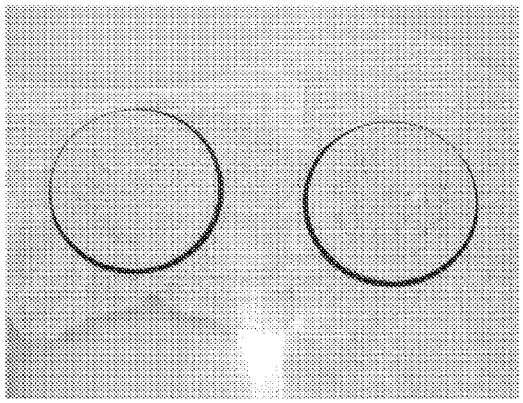
1. Infected sand flies were placed in Plexiglas feeders with a meshed surface to allow sand flies to feed through
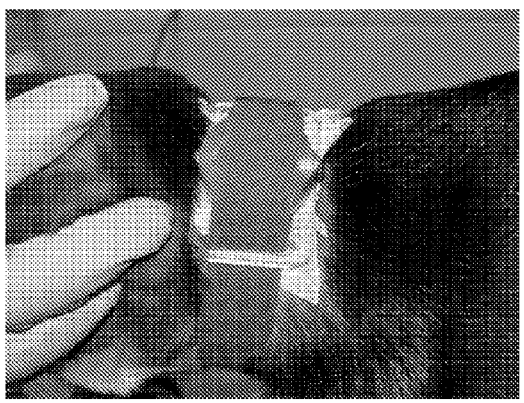
2. Each feeder was equipped with a Velcro belt to firmly hold the apparatus against the skin of the dogs
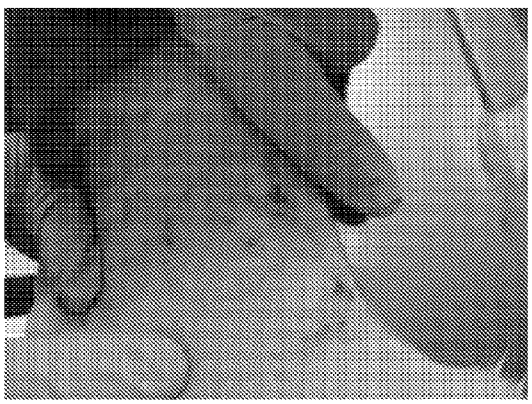
3. A minor reaction in the skin was observed at the bite site immediately after transmission

FIG. 5 (1/4)
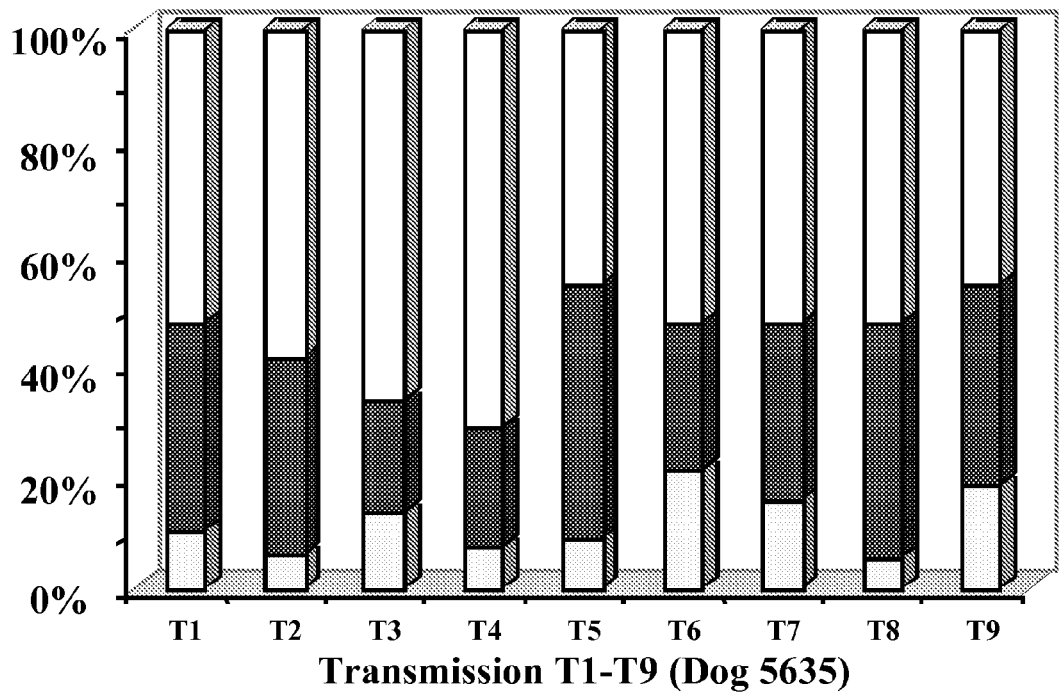
Transmission T1-T9 (Dog 5635)
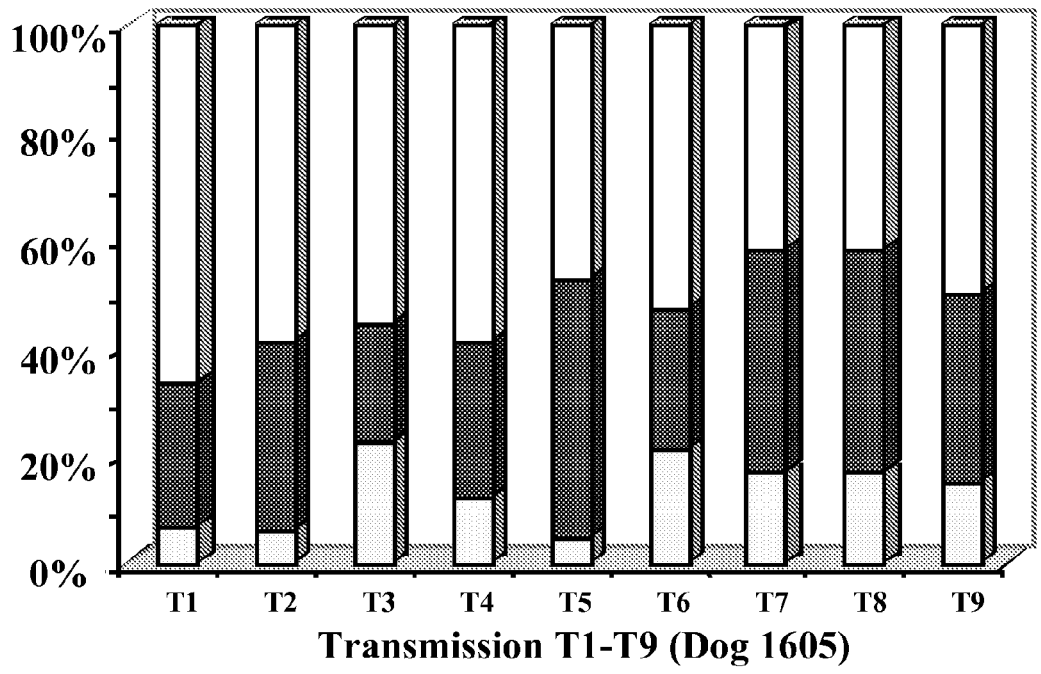
Transmission T1-T9 (Dog 1605)
■ Fed sand flies   □ Numerous metacyclics

FIG. 5 (2/4)
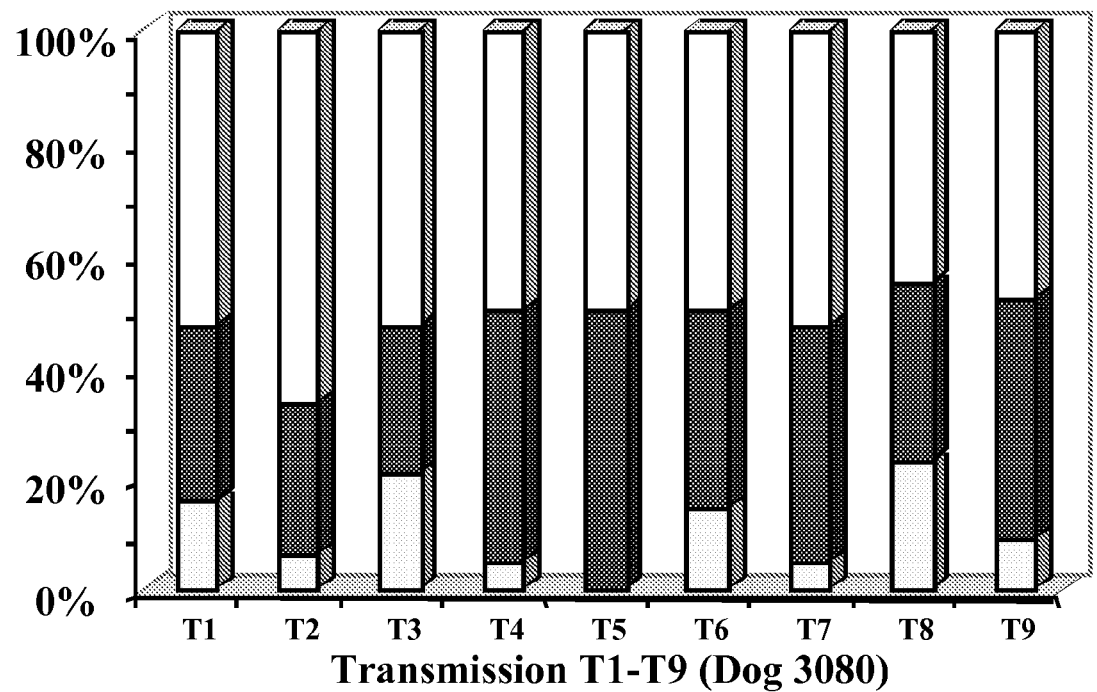
Transmission T1-T9 (Dog 3080)
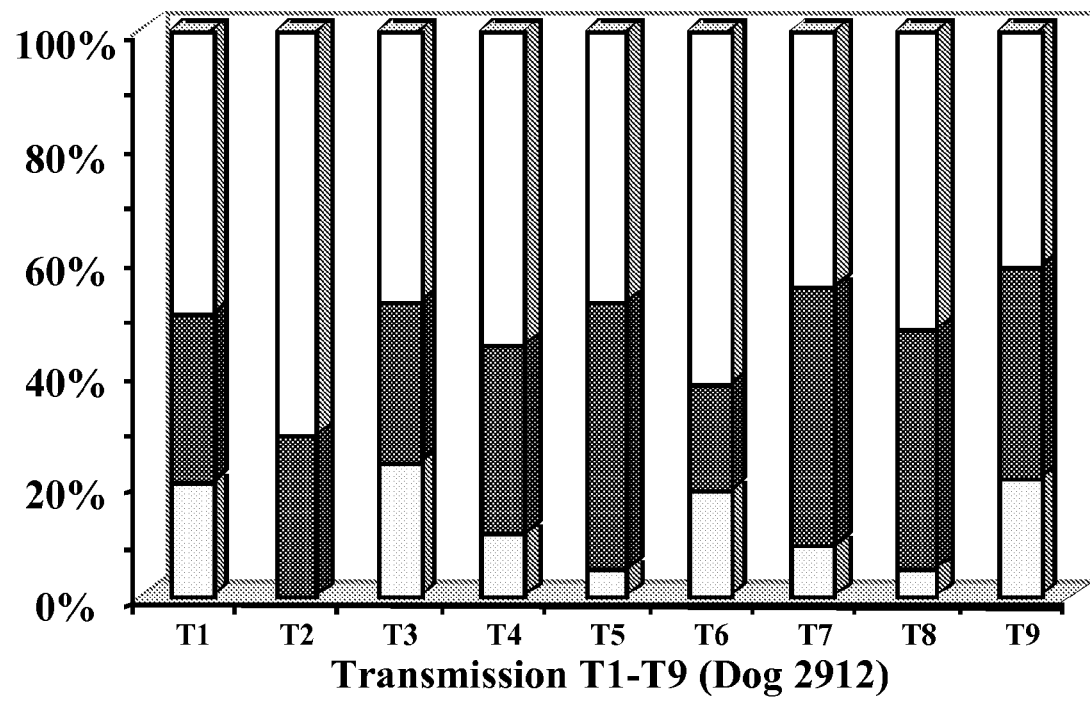
Transmission T1-T9 (Dog 2912)

FIG. 5 (3/4)
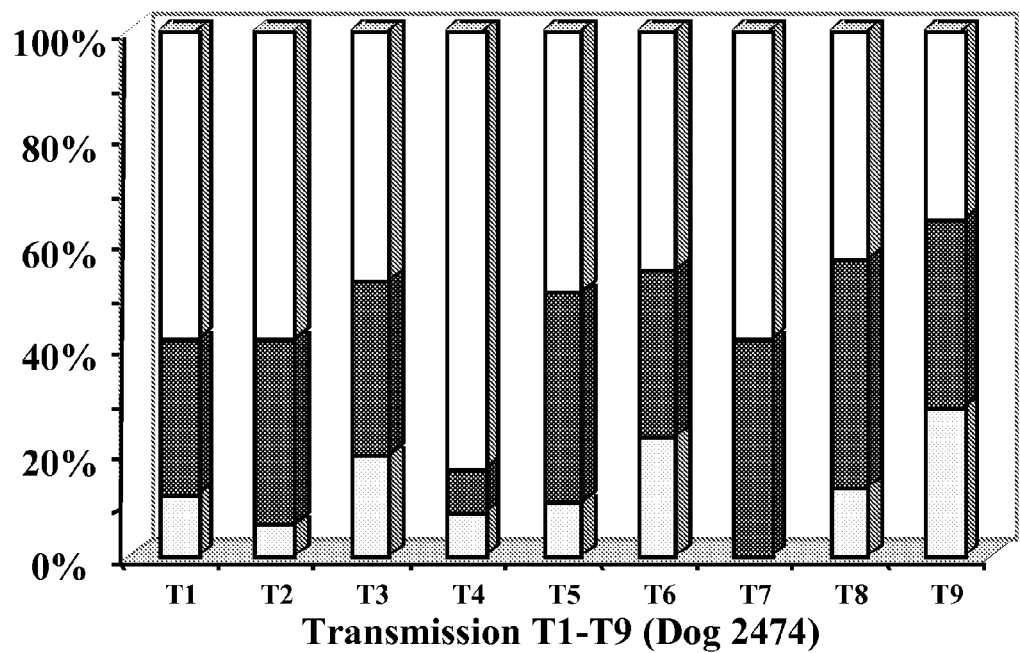
Transmission T1-T9 (Dog 2474)
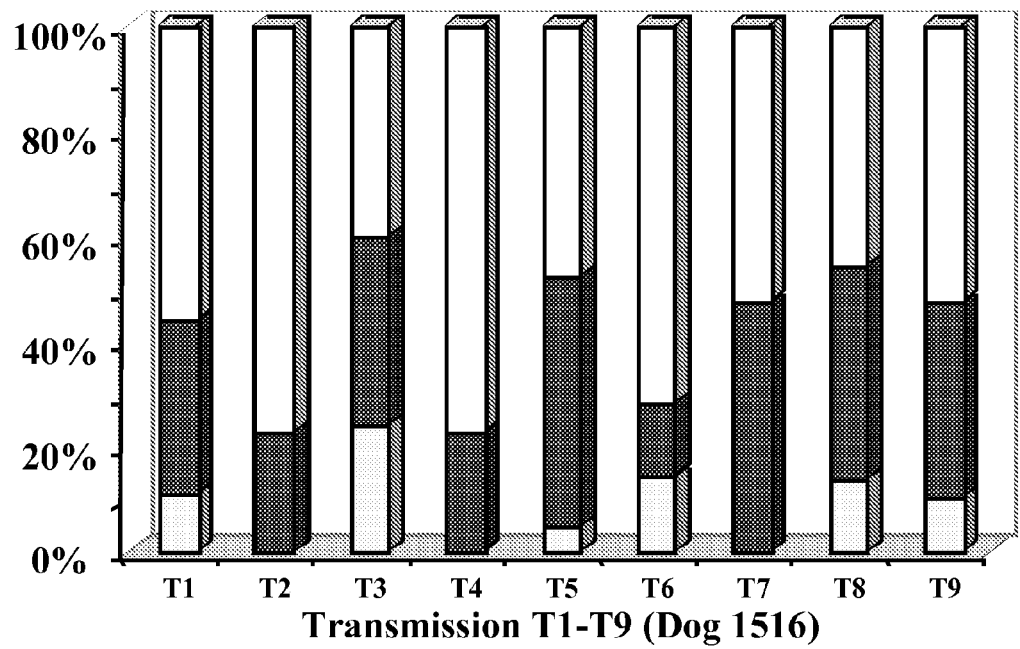
Transmission T1-T9 (Dog 1516)

FIG. 5 (4/4)
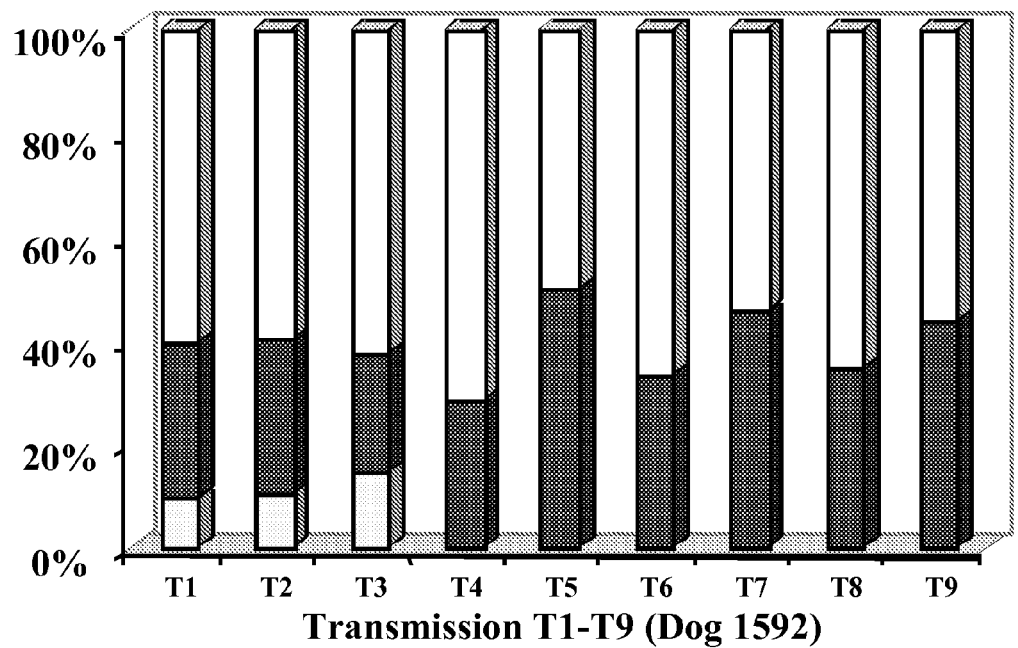
Transmission T1-T9 (Dog 1592)
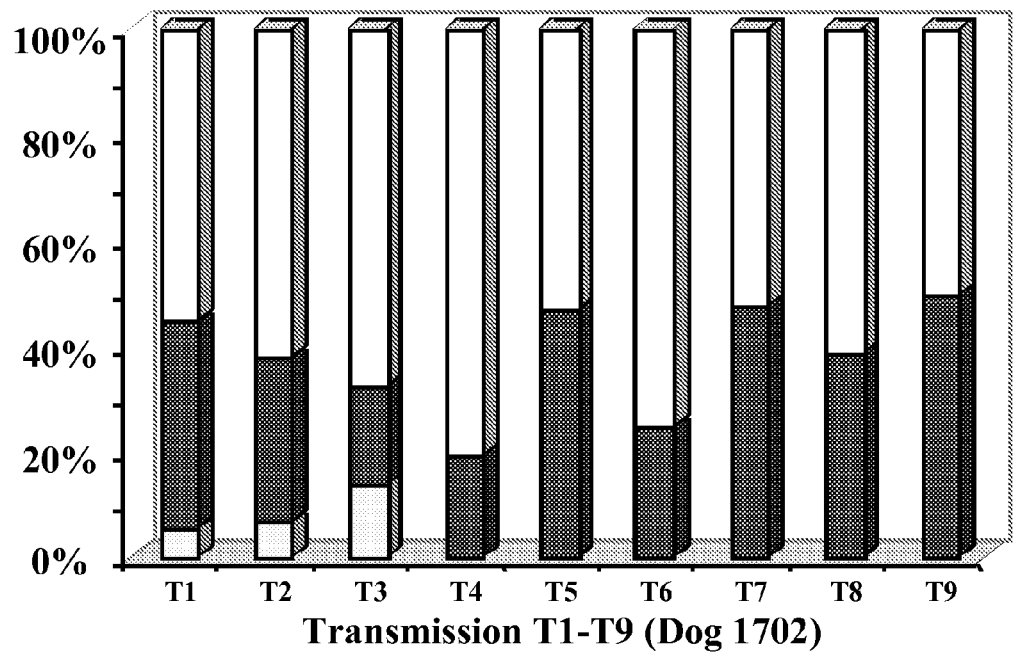
Transmission T1-T9 (Dog 1702)

FIG. 7

| | OD 405nm | |
|---|---|---|
| | DAY 0 | 3 MO |
| DOG 1516 | 0.054 | 0.510 |
| DOG 3080 | 0.056 | 0.393 |
| DOG 2474 | 0.041 | 0.377 |
| DOG 1702 | 0.051 | 0.344 |
| DOG 5635 | 0.060 | 0.334 |
| DOG 1605 | 0.064 | 0.284 |
| DOG 1592 | 0.032 | 0.249 |
| DOG 2912 | 0.047 | 0.177 |

Dogs exposed to 50 flies (high dose)

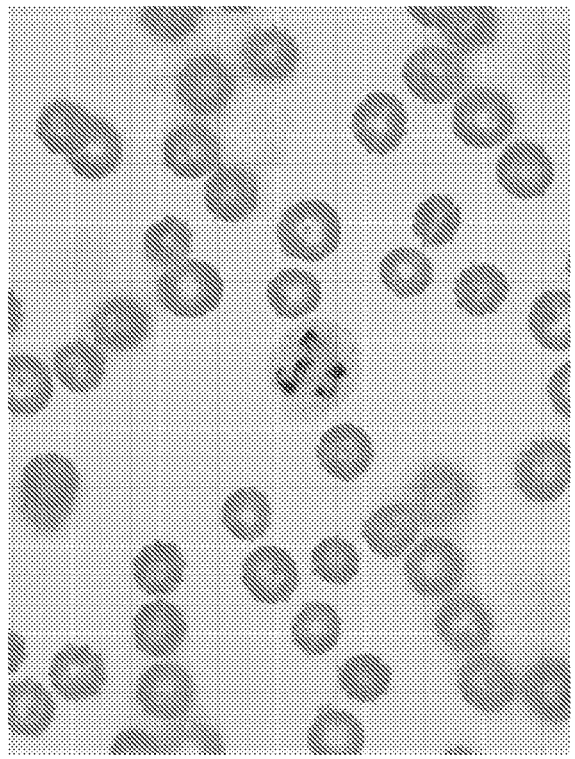
DOG 3080
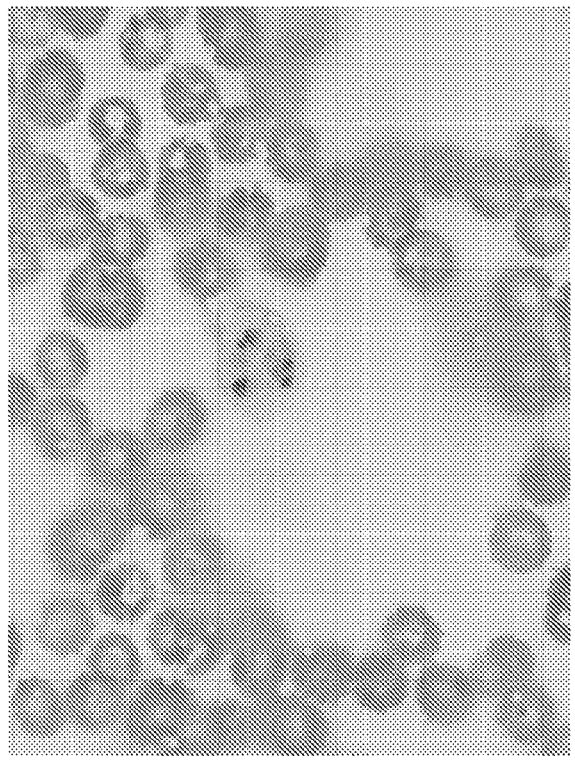
DOG 1516
FIG. 8

FIG. 12 (1/2)
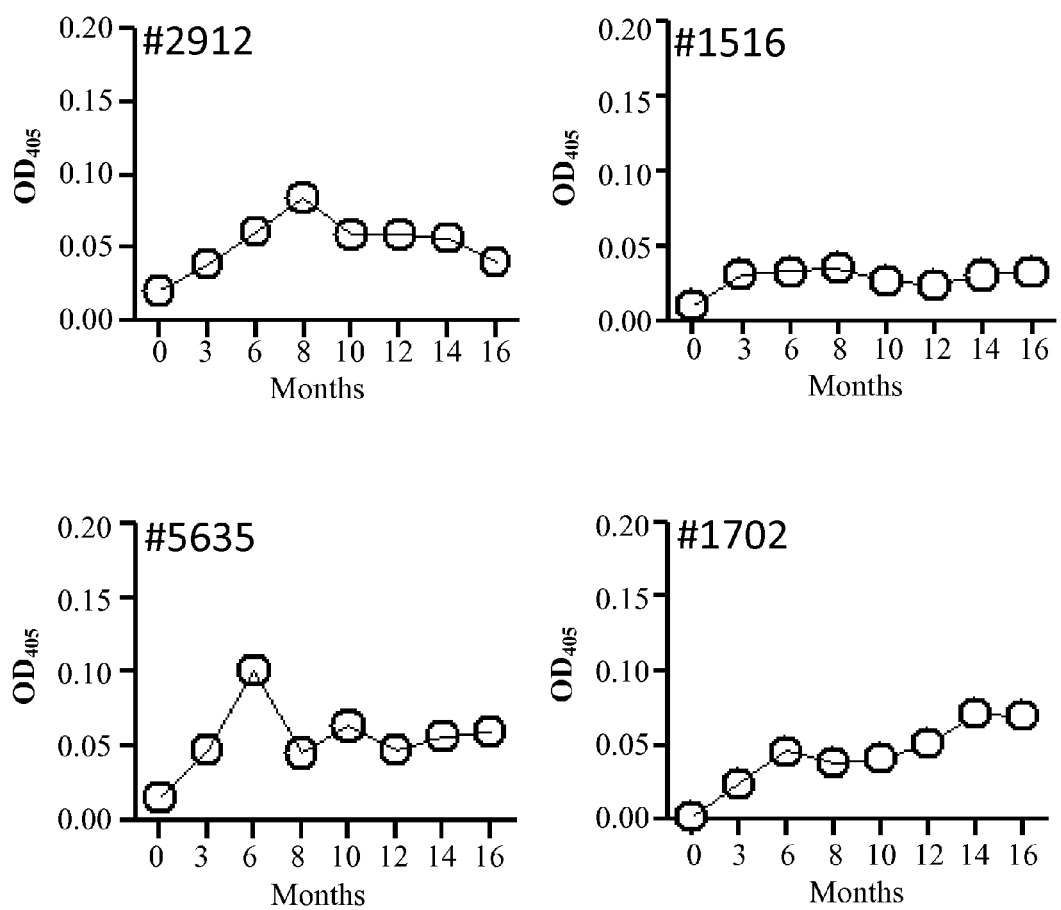

FIG. 12 (2/2)
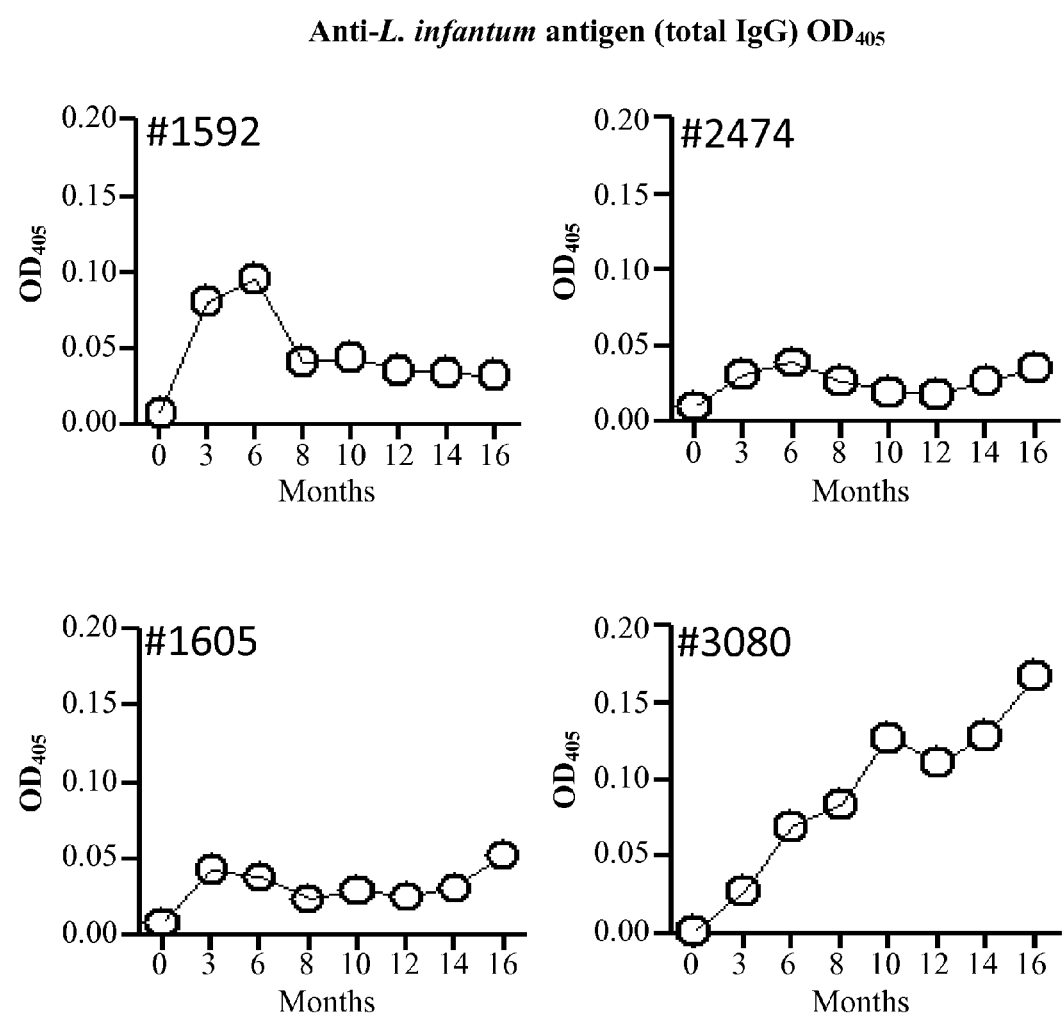

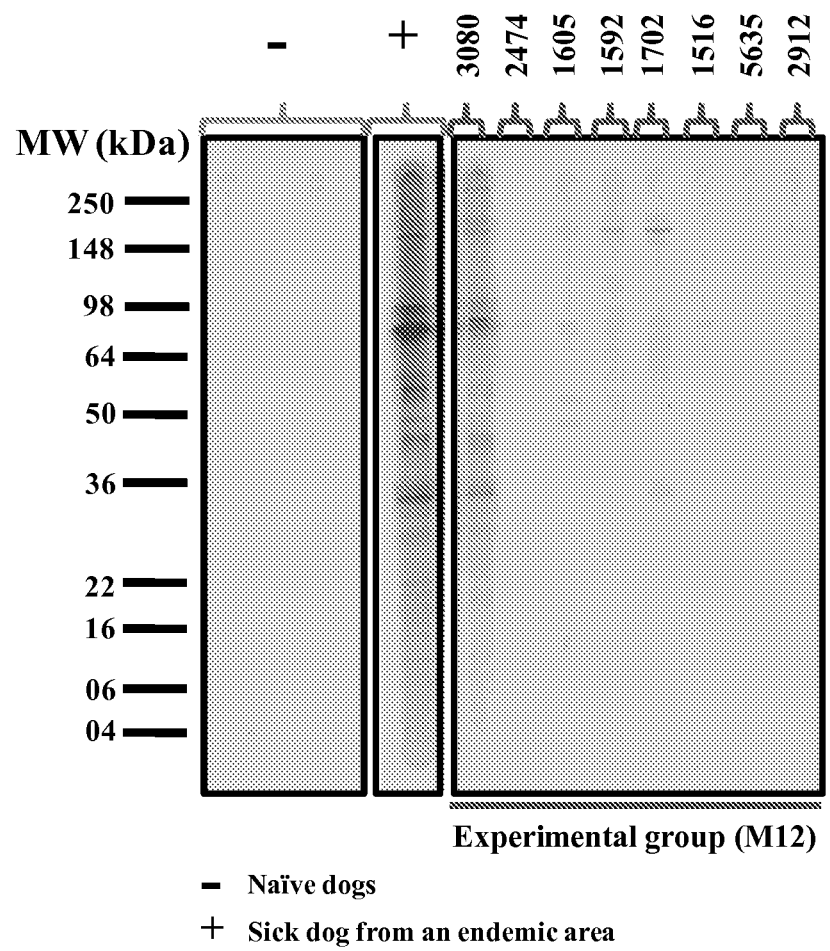

FIG. 14

| Dog ID | M0 | M3 | M6 | M8 | M10 | M12 | M14 | M16 |
|---|---|---|---|---|---|---|---|---|
| 1516 | - | - | - | - | - | - | - | - |
| 1592 | - | - | - | - | - | - | - | - |
| 1605 | - | - | - | - | - | - | - | - |
| 1702 | - | - | - | - | + | + | + | + |
| 2474 | - | - | - | - | - | - | + | - |
| 2912 | - | - | + | + | - | - | + | - |
| 3080 | - | - | + | + | + | + | + | + |
| 5635 | - | - | + | + | - | - | - | - |

M: Month

FIG. 15

FIG. 16

From M12 to M16 – Original site of transmission, and other skin lesions

20 *Lulo* sand flies on a shaved neck, paw or other skin lesions

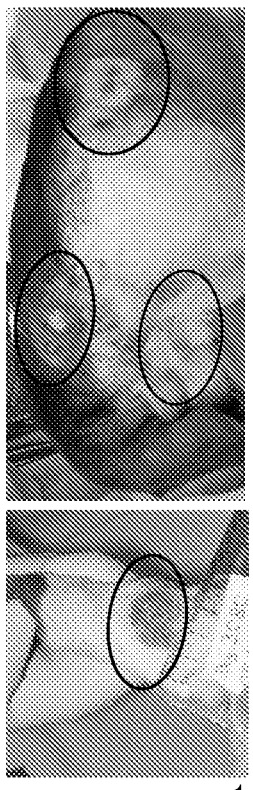

A

→ pick-up from DOG 3080

From M3 to M16 – Normal skin

20 *Lulo* sand flies on a shaved belly on a bi-monthly basis

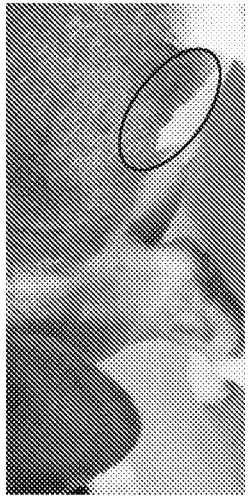

B

→ Zero pick-up !

% Pick-up from neck (original site of transmission): 33 %

% Pick-up from alopecia/skin lesions: 46%

% Pick-up from paw lesions: 73%

% Pick-up from belly (normal skin): 0 %

LEISHMANIA CHALLENGE MODEL

INCORPORATION BY REFERENCE

This application claims priority to U.S. provisional patent application No. 61/415,212, filed Nov. 18, 2010, the disclosure of which is herein incorporated by reference in its entirety.

FIELD OF THE INVENTION

The present invention relates to the development of a reproducible model for infection of dogs with *Leishmania infantum* via bites of vector sand flies, the natural mode of transmission.

BACKGROUND OF THE INVENTION

Leishmaniasis is a major and severe parasitic disease that affects humans, canines (dogs, wolves, foxes, coyotes, jackals), and to a lesser degree, felines (lions, tigers, domestic cats, wild cats, other big cats, and other felines including cheetahs and lynx).

*Leishmania Leishmania* and *Leishmania Viannia* subgenera are grouped into complexes of species and subspecies based upon molecular, biochemical and immunological similarities. There are several forms of the disease named by their clinical presentation including cutaneous, mucocutaneous or visceral leishmaniasis. Each of these forms of disease is caused by different species of sand flies found in different regions of the world. Cutaneous leishmaniasis of humans is associated with members of *L. major*, *L. tropica* and *L. aethiopica* complexes in the Old World and *L. mexicana* and *L. braziliensis* complexes in the New World. Visceral leishmaniasis is caused by *L. donovani* and *L. infantum* in Old World regions and by *L. infantum* in the New World. *L. infantum* is the primary agent associated with canine leishmaniasis.

The agent of visceral leishmaniasis is a protozoan parasite and belongs to the *Leishmania donovani* complex. This parasite is widely distributed in temperate and subtropical countries of Southern Europe, Africa, Asia, South America and Central America (Desjeux P. et al.). *Leishmania donovani infantum* (*L. infantum*) is responsible for the feline and canine disease in Southern Europe, Africa, and Asia and South and Central America. In humans, the agent is *Leishmania donovani donovani* (*L. donovani*), which is also related to *L. infantum*.

Sand flies of the genus *Phlebotomus* (Old World) and *Lutzomyia* (New World) are the primary vectors responsible for disease transmission. Currently these are the only known vectors capable of spread; fleas, ticks and other arthropods have not been shown to be competent vectors. However, rare cases of leishmaniasis have been contracted through exchange of blood or body fluids, direct contact and at least one case of congenital transmission. *P. ariasi*, *P. perniciosus* and *P. neglectus* are the most common carriers in Southern Europe, Africa, and Asia, whereas *Lu. longipalpis* is the most common carrier in Southern and Central America.

Canine leishmaniasis is a slowly progressive disease that can take up to 7 years to become clinically apparent (McConkey S E et al.; Slappendel R J et al.). Even then, signs are frequently nonspecific and a diagnosis of *Leishmania* is seldom considered. Dogs are most commonly infected with *L. infantum* (*L. donovani* complex) which is responsible for viscerotropic disease in people. However, up to 90% of infected dogs present with both visceral and cutaneous lesions (Slappendel R J et al.). On the other hand, many dogs appear naturally resistant to this parasite and may remain asymptomatic despite known infection (Grosjean N L et al.). It is estimated that only 10% of dogs residing in endemic areas actually develop clinical disease (Lindsay D S et al.). This lower incidence of clinical disease is attributed to a genetic predisposition of certain dogs to mount a more protective cell-mediated immune response than a humoral response (Lindsay D S et al., McConkey S E et al., Slappendel R J, et al.). Furthermore, it has been reported that up to 20% of infected dogs may mount an adequate immune response and spontaneously recover from clinical illness (McConkey S E et al.). In animals that mount a humoral response, IgG1 appears to correlate with clinical disease while asymptomatic dogs have higher IgG2 antibody levels (Lindsay et al.).

Some of the more frequently reported clinical signs of leishmaniasis include listlessness, fatigue and exercise intolerance coupled with anorexia and weight loss that eventually culminate as wasting disease (McConkey S E et al.). These signs may or may not be accompanied by fever, local or generalized lymphadenopathy (90%) and/or hepatosplenomegaly (Grosjean N L et al., Lindsay D S et al., McConkey S E et al., Martinez-Subiela S et al.). Articular involvement is also fairly common and may present as lameness with swollen joints or simply as a stiff gait. Less common findings include ocular lesions (<5%), chronic diarrhea (30%) and long, deformed brittle nails (20%) referred to as onychogryphosis (Lindsay D S et al., Slappendel R J et al.). Cutaneous lesions are present in up to 89% of infected dogs, with or without overt signs of visceral involvement. Lesions of cutaneous leishmaniasis may occur anywhere on the body but the most common sites are those which are exposed to the environment and are therefore more susceptible to bites from the sand flies. The initial papule rapidly gives rise to an ulcer. Visceral leishmaniasis is invariably fatal if not treated promptly. Visceral leishmaniasis affects the internal body organs, specifically the spleen and the liver.

Dogs are considered the major reservoir of leishmaniasis. The disease is characterized by chronic evolution of viscerocutaneous signs occurring in less than 50% of infected animals (Lanotte G. et al.). Both asymptomatic and symptomatic dogs with detectable antibodies may be infectious (Molina R. et al.; Courtenay O. et al.). Cats may also be carriers of the protozoan parasites and are thus considered secondary potential reservoirs.

Due to a number of factors, treatment options for leishmaniasis in dogs and response to therapy are limited at best. For some undefined reason, visceral leishmaniasis is more difficult to treat in dogs than in humans. No treatment option is 100% effective in clearing parasitic infection and clinical disease often reappears with cessation of therapy (Lindsay D S et al.). In endemic areas, the most common treatment regimen has been a combination of allopurinol with a pentavalent antimonial such as meglumine antimonite or sodium stibogluconate (Lindsay D S et al., Slappendel R J et al.). However, in recent years this protocol has fallen out of favor due to increasing resistance of the parasite to the drug as well as adverse side effects associated with these compounds (Lindsay D S et al.). To further limit treatment options, Pentostam® (sodium stibogluconate) is the only available antimonial in the United States and its distribution is regulated by the Centers for Disease Control and Prevention (CDC) in Atlanta, Ga. (Lindsay D S et al.).

Mass detection of seropositive dogs followed by culling and/or drug treatment, or the mass application of deltamethrin-impregnated collars, was shown to have an impact in reducing human and canine Leishmaniasis prevalence in endemic areas of Southern Europe, Africa, and Asia (Maroli M. et al. Mazloumi Gavgani A. S. et al.), although the efficacy of eliminating seropositive canines has been debated (Dietze R. et al.; Moreira Jr. E. D. et al.). These control measures are either considered unacceptable, expensive or not effective (Gradoni L. et al.). Mathematical models used to compare the effectiveness of various tools for controlling Leishmaniasis suggest that a canine vaccine may be the most practical and effective method (Dye C.). Therefore, the development of vaccines able to protect canines from Leishmaniasis and/or to prevent disease progression in infected animals is highly desirable for the implementation of Leishmaniasis control programs as well for the veterinary community (Gradoni L. et al.).

However, to date, no vaccine is available for the treatment of *Leishmania* infection in dogs. The reproducible model of infection of dogs by sand fly bites described in the present invention provides a platform to investigate the efficacy of promising vaccines and will fulfill a long-felt gap in the art. Considering the complexity of canine visceral leishmaniasis, including its chronicity and our lack of understanding of the factors governing virulence and visceralization of *Leishmania* parasites, the establishment of a protocol for a controlled reproducible visceral infection in dogs that reflects the clinical picture observed in the field represents a valuable tool to undertake vaccine studies, both prophylactic and therapeutic. Importantly, due to the unpredictability of a sand fly transmission season which is influenced by factors such as weather, this transmission model would constitute a significant reduction in cost and a major improvement in study outcomes.

Models for the transmission of parasites by bites of infected sand flies have been established for cutaneous leishmaniasis in mice (Kamhawi et al., 2000; Nathan et al., 2008) and non-human primates (Lawyer et al., 1990; Probst et al., 2001). However, it has been much harder to develop models of transmission by bite for visceral disease. Most models of visceral leishmaniasis rely on the injection of a large number of parasites intravenously or via the intracardiac route (Melby et al, 2001; Wilson et al., 2005). A distinct feature of human leishmaniasis is its polymorphic nature where different parasite species, and for certain species including *L. infantum* different strains, cause a spectrum of clinical manifestations ranging from asymptomatic, to contained cutaneous infection, to visceral disease (Gradoni & Gramiccia, 1994; First WHO report on neglected tropical diseases, 2010). To date, the factors governing parasite tropism are poorly understood and are thought to be a combination of the genetic susceptibility of the host, virulence of the parasite strain and the immune status of the host. This has likely contributed to the difficulty of developing a model of visceral leishmaniasis by bite of infected sand flies which remains unavailable to date even for small animal models such as mice and hamsters.

More recently, models using intradermal injection with a large number of infectious parasites have been developed (Dondji et al, 2005; Wilson et al., 2005; Gomes et al., 2008). These models however do not resemble the natural mode of infection by sand fly bite where the parasite inoculum is considerably smaller (Kimblin, 2008) and where the transmission event involves the presence of salivary proteins and parasite secretory gel among others, both reported as exacerbating the outcome of disease (Titus & Ribeiro, 1988; Morris et al; 2001; Rogers et al., 2004). Of additional importance, Peters et al. (2009) demonstrated that protection from cutaneous leishmaniasis, observed against needle challenge in vaccinated mice was abrogated by transmission via infected bites. This highlights the importance of using a natural challenge by vector sand fly bites in vaccine-related studies particularly in dogs which are the target animals for canine vaccines.

Taken together, the body of evidence points to a serious and long-felt need for a method that models *Leishmania* infection, as it occurs naturally in the field (i.e. via the bites of *Leishmania*-infected sand flies). However, until the instant invention, no one has been able to solve this challenging problem.

SUMMARY OF THE INVENTION

The present invention provides a method for effectively and reproducibly infecting canines with *Leishmania infantum* using sand flies to vector the parasite. The inventive method comprises several steps, including:

1) testing canines for previous exposure to sand fly salivary proteins or to *Leishmania* antigens to ensure their naïve status;

2) implementing multiple transmission events (to naïve canines) using 10-50 bites from *L. infantum*-infected sand fly, wherein the *L. infantum* is a virulent strain isolated from a sick canine, and wherein the sand flies are "transmitting sand flies", identified according to well-characterized features, wherein the implementing comprises applying infected sand flies to multiple sites on the dogs to mimic what occurs under field conditions; and 3) scoring sand flies (i.e. counting parasite load) post-transmission to verify the success of transmission.

The invention also provides *Leishmania* spp.-infected sand flies, and stable colonies thereof, for use in practice of the infection method.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 3 provides graphs for pre-transmission sand fly scoring of the parasite load and percent metacyclics per fly gut. Before each transmission, 5 to 10 flies were dissected and the status of the infection scored to estimate the projected transmission-efficiency;

FIG. 4 depicts multiple transmission of *Leishmania* to dogs via infected sand fly bites. Transmitting flies fed through a mesh surface on two sites of a shaved dog neck;

FIG. 5 provides graphs of Post-transmission sand fly scoring. Sand flies used in transmission events were scored carefully to assess feeding success and presence of metacyclics;

FIG. 7 depicts anti-*Leishmania* antibodies in dogs infected with *Leishmania infantum* by *Lutzomyia longipalpis* bites, three months post transmission;

FIG. 8 depicts smears from spleen aspirates of two of the infected dogs showing amastigote-like bodies three months after transmission;

FIG. 12 depicts post-transmission kinetics of anti-*Leishmania* antibodies by ELISA in dogs infected with *Leishmania infantum* by *Lutzomyia longipalpis* bites over time FIG. 13 depicts Western blot showing the recognition of multiple *Leishmania* antigens in experimentally infected dogs. Dog 3080 shows a response comparable to that of a sick dog from an endemic area.

FIG. 14 depicts live parasite isolation from viscera of dogs over time following infection with *Leishmania infantum* by *Lutzomyia longipalpis* bites FIG. 15 picture of *Leishmania infantum* lesions in dogs infected by *Lutzomyia longipalpis* bites manifesting in various parts of the body including dorsal neck lesions (A) and bi-lateral paw lesions (B) characteristic of sick dogs from endemic areas.

FIG. 16 depicts parasite pick-up by uninfected sand flies from original site of transmission and from skin lesions manifesting in other parts of the body (A). Sand flies did not pick-up parasites from normal skin by xeno-diagnosis carried out on bi-monthly basis (B).

DETAILED DESCRIPTION OF THE INVENTION

Figure 1:
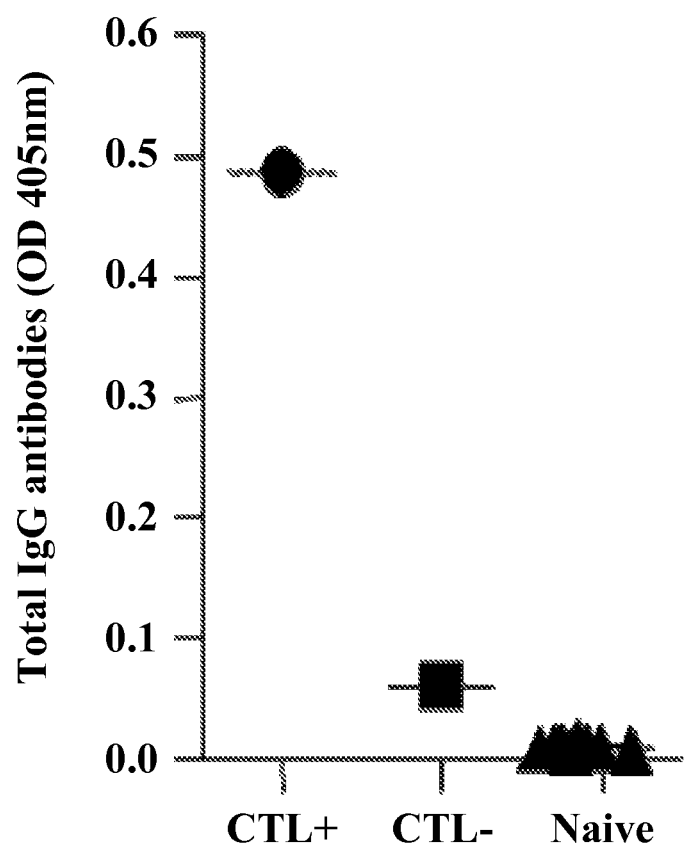
FIG. 1 provides graph of results of testing dogs for previous exposure to sand fly salivary proteins; total IgG antibodies, as measured by ELISA ($OD_{405}$), is indicated for positive and negative controls as well as Naïve dogs.

The present invention provides a novel method for modeling natural *Leishmania* infection in canine animals. The inventive method is effective for mimicking natural *Leishmania* infection in canines for the evaluation, for example, of the efficacy of anti-*Leishmania* biologicals, such as vaccines, or anti-*Leishmania* pharmaceutics, such as antiparasiticides and/or antiprotozoals.

Development of the infection model described herein required several technical optimizations. Applicants had previously attempted to infect dogs under the following conditions: six two-year-old female dogs were subjected to bites of 50 *Lu. longipalpis* sand flies infected with our laboratory strain of *L. infantum*. Transmission took place once at 10 days post-infection on one site of the dogs' shaved neck. On average, 16-18 flies per dog showed evidence of feeding by the sand flies indicative of parasite transmission. All dogs showed physiological changes within the first two weeks following transmission. Thereafter, the dogs stabilized and did not show any clinical symptoms of disease. Here, Applicants have optimized the model aiming to establish the conditions required for a reproducible clinically patent infection in the dogs following transmission of *L. infantum* by bites of vector sand flies.

In one embodiment, the method comprises the steps of:
1. testing the canine animals to ensure they are free of *Leishmania* and previous exposure to sand fly salivary proteins;
2. transmitting the *Leishmania* parasite to the canines by means of *Leishmania*-infected sand fly bites; and
3. scoring sand flies post transmission to verify success of transmission, thereby infecting the canine animals.

In another embodiment, the method comprises the steps of:
1. selecting canines six months or younger for infection;
2. testing the canines for previous exposure to sand fly salivary proteins;
3. infecting vector sand flies with a virulent isolate of *L. infantum* or other *Leishmania* spp., obtained from a canine infected with the *L. infantum* or other *Leishmania* spp., wherein only passages 5 or 4 or 3 or earlier of the *L. infantum* or other *Leishmania* spp. are used to carry out the infection, and wherein the infecting is accomplished by supplying the sand flies with blood containing *L. infantum* or other *Leishmania* spp.;
4. monitoring the sand fly infection to follow the progression of the infection along the sand fly midgut;
5. assessing the state of bacterial colonization in the sand fly;
6. assessing an incremental increase in total parasite number with time and an incremental increase in appearance of metacyclics with time;
7. scoring sand flies prior to every transmission event;
8. infecting groups of flies 1 or 2 or 3 times a week;
9. carrying out on multiple sites over multiple transmissions of *Leishmania* spp. to dogs via sand fly bites; and
10. scoring (i.e. quantification of parasite load/fly and % of metacycles/fly) of sand flies used for transmission to assess feeding success and infection status, thereby modeling naturally occurring *Leishmania* infection in canines.

In an embodiment, the present invention relates to the development of a reproducible model for infection of dogs with *Leishmania infantum* by bites of vector sand flies, the natural mode of transmission. Dogs are infected under controlled laboratory conditions using a protocol involving several steps: 1—Use young male dogs 6 months or younger; 2—test dogs for previous exposure to sand fly salivary proteins or to *Leishmania* antigens to insure their naïve/pathogen-free status; 3—use a recent virulent strain of *L. infantum* from a sick dog; 4—use only 'transmitting sand flies' identified according to well-characterized features representing a superior mature infection, a requirement for successful transmission; 5—undertake multiple transmission events with 10-50 infected sand fly bites, mimicking recurrent exposure to infected flies over a transmission season; 6—apply infected sand flies to multiple sites on the dogs to mimic what occurs under field conditions; 7—score sand flies post-transmission to verify the success of transmission.

Example 1

Infection of Beagles Using *Lu. longipalpis* Vector Sand Flies

A total of eight Beagles were infected by 10-50 infected *Lu. longipalpis* vector sand flies using a stringent protocol to ensure a reproducible infection in dogs. The following steps were taken:

1. Selected male Beagles six months or younger for infection. Test the dogs for previous exposure to sand fly salivary proteins, here *Lu. longipalpis*, using ELISA (FIG. 1).

2. Infected vector sand flies, here *Lu. longipalpis*, with a recent virulent isolate of *L. infantum*, obtained from a sick dog. This is a vital step as the parasites lose virulence for dogs after passage in the laboratory; parasites beyond 3 passages in culture will not be used.

Figure 2:
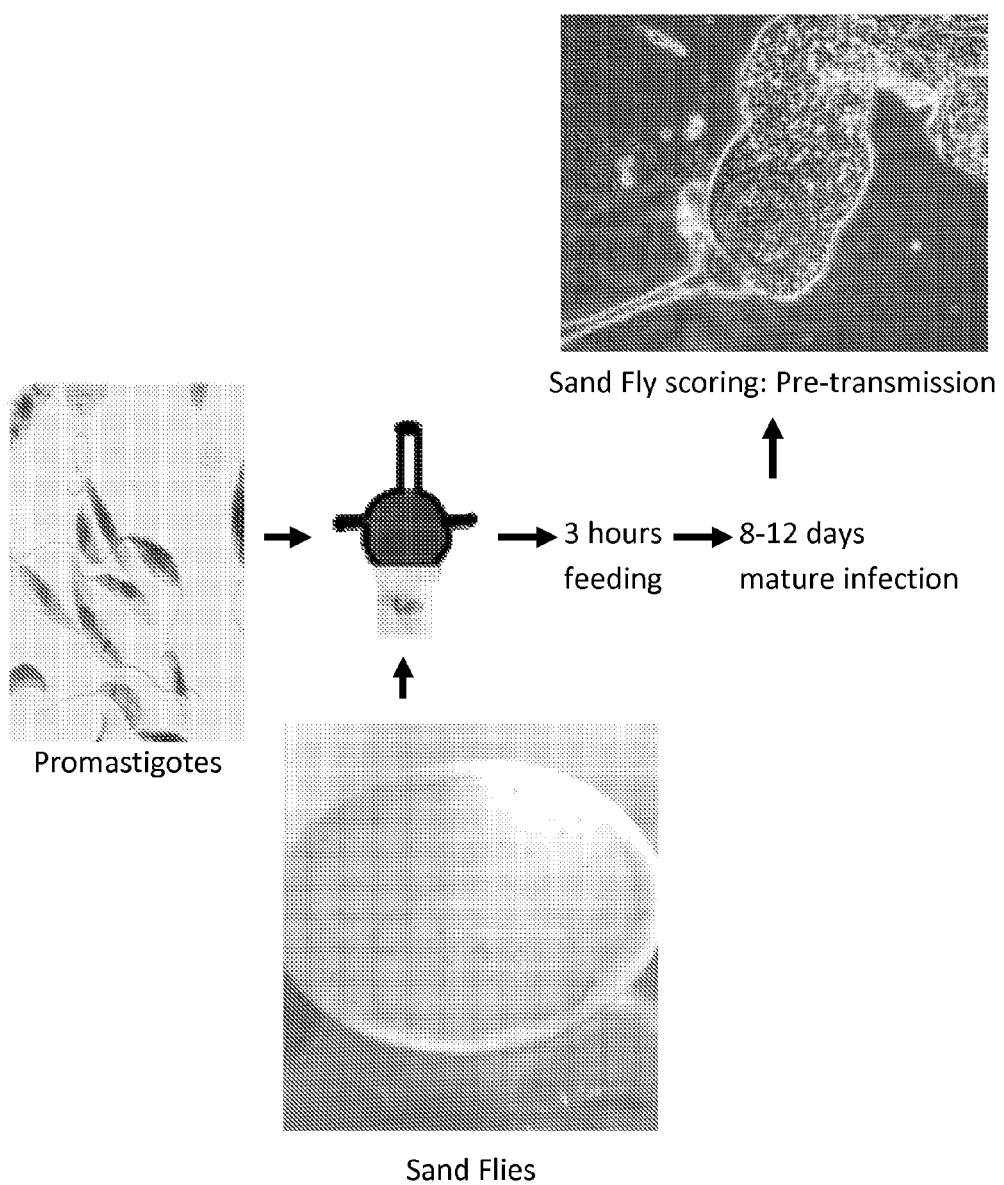
FIG. 2 provides a flow diagram—*Lutzomyia longipalpis* sand flies were infected with blood containing up to 4 million parasites per ml using a membranous reservoir apparatus with a virulent *L. infantum* (from a sick dog; only passages 1-3 only were used). Up to 5 million procyclic promastigotes were present per ml of heparinized mouse blood.

3. Sand flies were infected with blood containing up to 4 million parasites per ml using a membranous reservoir apparatus (FIG. 2).

4. Monitored the sand fly infection over 10-12 days, on days 2, 7, 10 and 12 to follow the progression of the infection along the sand fly midgut. The infection was assessed for low bacterial colonization, an incremental increase in total parasite number with time and an incremental increase in appearance of metacyclics. Sand flies were scored carefully prior to every transmission event (FIG. 3). Groups where infected flies showed a mean parasite load of ≧30,000 and a mean percent metacyclics of ≧50% or more were considered "excellent transmitting flies". Groups of flies were infected three times a week to ensure mature infection were available for use in transmissions.

5. Carried out multiple transmissions to dogs to mimic what occurs in the field over a transmission season. Transmission was carried out every 2-3 days (based on the infection status of flies) for a total of 6-8 transmissions were carried out over a period no longer than 2 weeks from the initial transmission event (FIG. 3). Transmitting sand flies were placed in custom-made secured Plexiglas feeders with a meshed surface to allow sand flies to feed through. Each feeder was equipped with a VELCRO® belt to firmly hold the apparatus against the skin of the dogs.

6. Carried out transmission on multiple sites. Six dogs were challenged with 10 infected sand flies, five on each of two sites (low dose) simultaneously to on a shaved neck and 2 dogs challenged with 50 infected sand flies, 25 on each of two sites on a shaved neck (high dose). Flies were kept in contact with the dogs for a period of 1.5 hours.

7. Post-transmission scoring (i.e. quantification of parasite load/fly and % of metacycles/fly) of sand flies used for transmission was carried out to assess feeding success and infection status. This step ensured the ability to map the overall transmission efficiency for each dog at the end of the protocol (FIG. 5).

Figure 6:
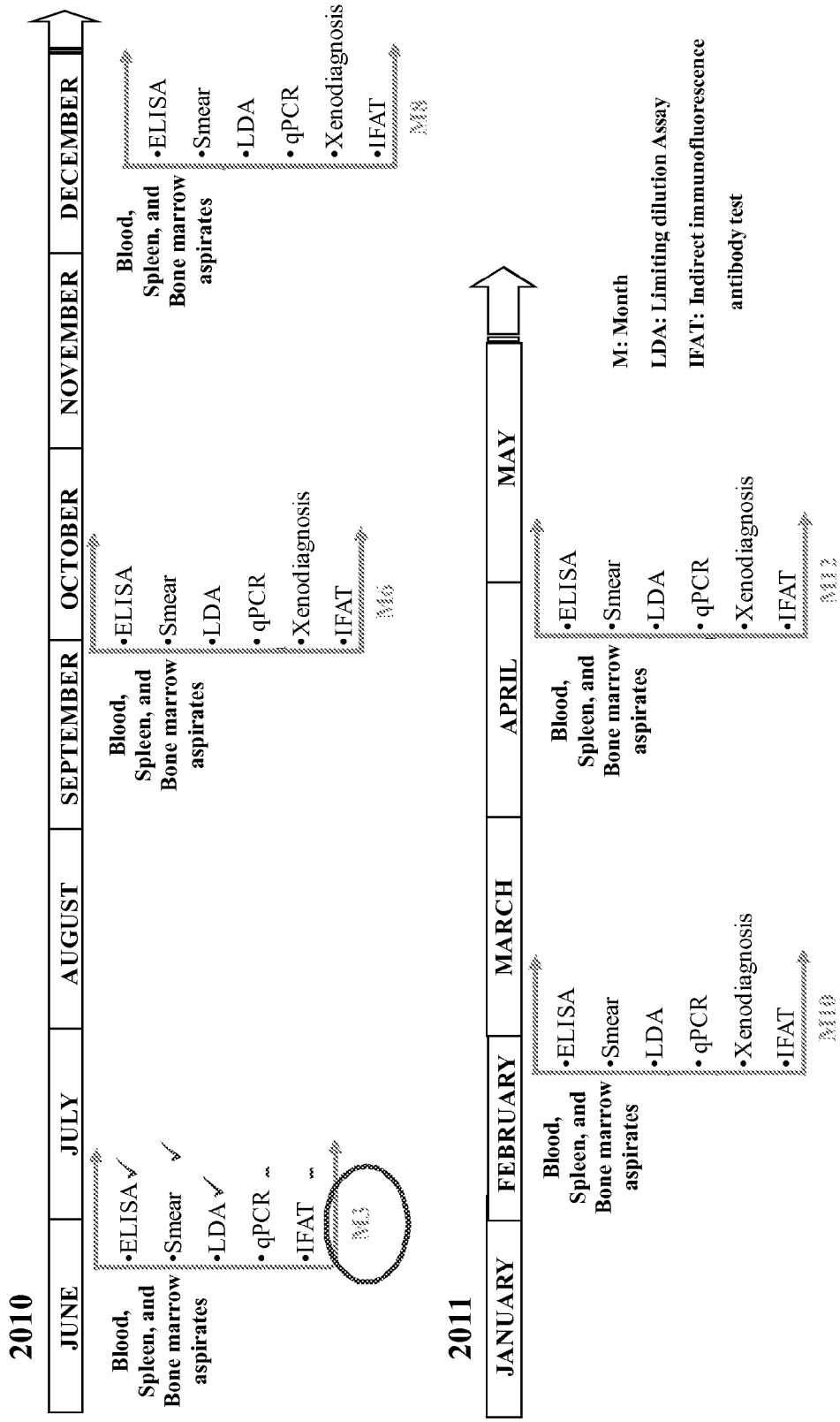
FIG. 6 presents a projected post-transmission follow-up of *Leishmania* infection in dogs.

Following completion of the transmission protocol, and considering the chronicity of the infection, follow-up of dogs was carried out every 3 months for the first two timepoints and then every other month thereafter (monitoring is ongoing as of the filing of this disclosure) (FIG. 6).

Figure 9:
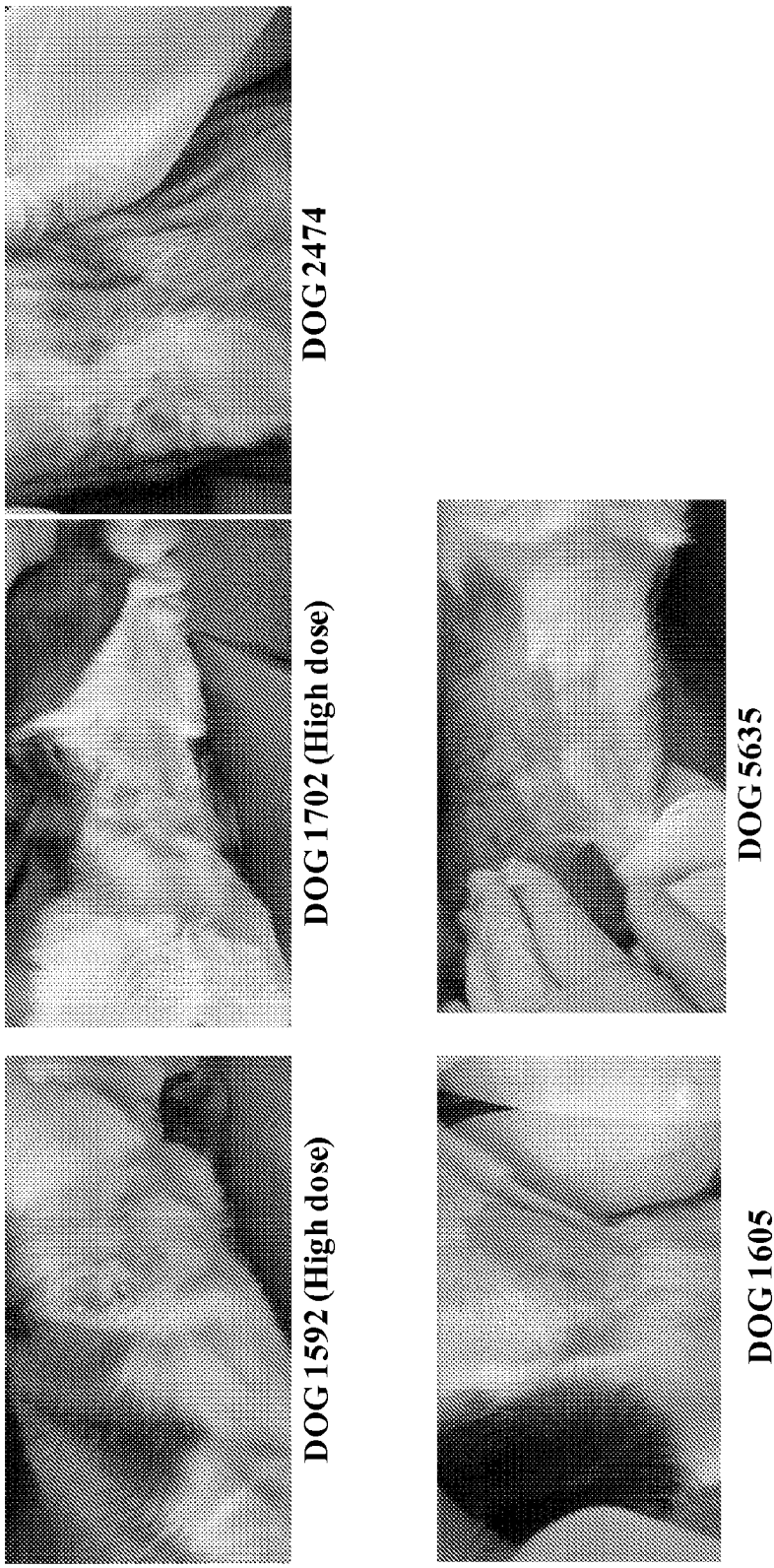
FIG. 9 depicts ulcerative skin lesions in the neck at the site of bites, the first clinical symptoms observed in dogs four months post transmission. Skin lesions are typically associated with canine visceral leishmaniasis.
Figure 10:
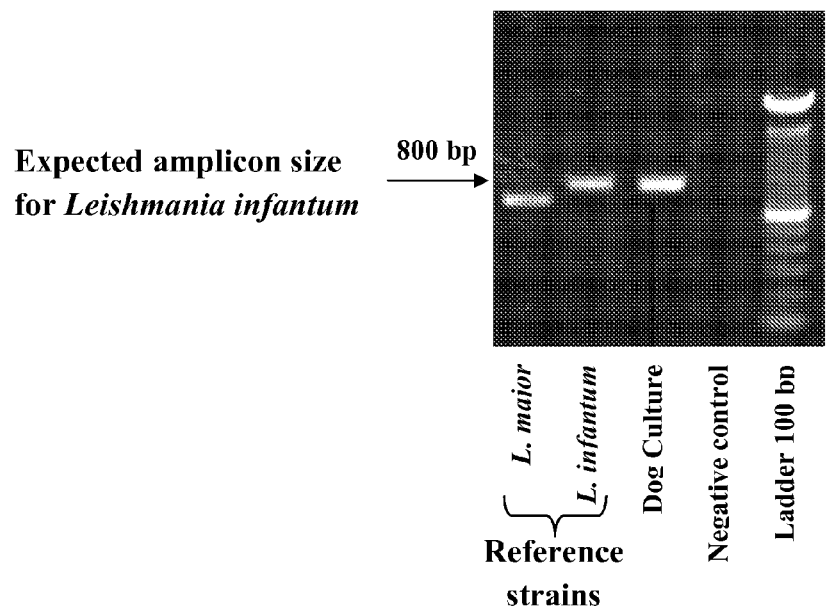
FIG. 10 depicts agarose gel picture of PCR products. Parasites cultured from a skin lesion in the neck of one of the dogs was confirmed as *Leishmania infantum* by PCR

All eight dogs showed a significant increase in their anti-Leishmania titer three months post transmission (FIG. 7). This was unexpected since this timepoint was considered too early compared to what is known from field studies. Spleen aspirates from two dogs showed amastigote-like bodies in the spleen, but cultures were negative (FIG. 8). Four months post transmission, six out of eight dogs (#3080, #1592, #1702, #1605, #5635, and #2724), including the two dogs exposed to 50 infected flies, developed skin regions at the site of bites (FIG. 9). Lesions were crusted; the skin was red and thick. Additionally, five of these dogs showed enlarged submandibular lymph nodes. Both cutaneous manifestations and enlarged lymph nodes are clinical signs typically associated with canine visceral leishmaniasis. Cultures taken from lesion tissue of all the dogs were positive for Leishmania. PCR of cultured parasites confirmed the species as L. infantum (FIG. 10). At this timepoint, spleen and bone marrow aspirates were negative in culture and PCR.

Figure 11:
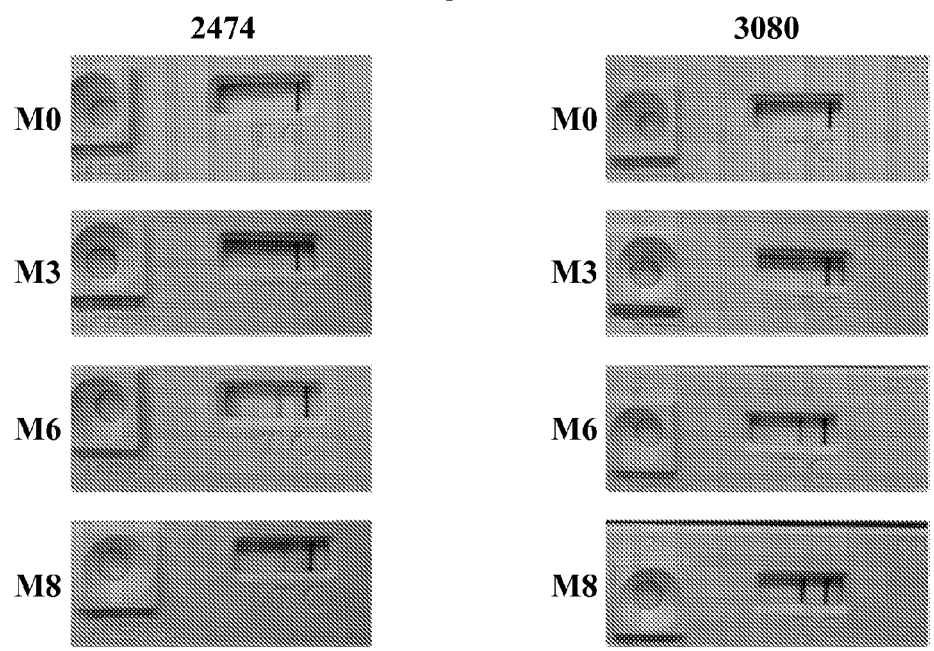
FIG. 11 depicts picture of a commercial rK28 strip test showing the increase in recognition of *Leishmania* antibodies over time in two representative dogs infected with *Leishmania infantum* by *Lutzomyia longipalpis* bites; dog 2474 had the weakest response and dog 3080 the strongest response.

Six months post transmission, an additional dog (#2912) developed superficial ulcerative skin lesions and five of the dogs (#3080, #1592, #1702, #2724, and #2912) continue to have multifocal small lesions at the sand fly bite sites (thick crusty areas). Importantly, three dogs had visceralizing parasites; cultures from dogs #3080 and #5635 were positive in cultures from bone marrow tissue and dog #2912 was positive in a culture from spleen tissue. Additionally, the submandibular lymph nodes remain swollen in five dogs, and one shows an additional enlargement of the popliteal lymph nodes. Biochemical and blood protein level tests carried out seven months post transmission show that dogs #1592 and #2474 were low on Magnesium and high for BUN/Creatinine ratio; dog #3080 was high on the BUN/Creatinine ratio; and dogs #1516 and #1702 were low on Magnesium. Using a commercial rK28 strip test, Applicants confirmed that all dogs had been infected by the parasites. FIG. 11 depicts two examples showing the strong antibody response to Leishmania up to eight months post transmission in dogs 2474 and 3080 (weakest and strongest responders, respectively).

Thereafter, the dogs were examined on a monthly basis. FIG. 12 shows the antibody titer of the eight dogs up to month 16 by ELISA. It demonstrates the fluctuation of the antibody response with time and highlights the chronic nature of leishmaniasis in dogs. Apart from dog 3080, the antibody titers were generally low, though in four dogs (#5635, #1702, #2474 and #1605) the titers were trending upward (FIG. 12). Western blot showed that most experimentally infected dogs recognized multiple Leishmania antigens, with dog 3080 showing a profile comparable to the positive control, a polysymptomatic sick dog from an endemic area in Brazil (FIG. 13). Parasite isolation by aspiration from the spleen and lymph nodes showed that overall, live parasites were isolated from the spleen of five of the eight dogs experimentally infected by bite (FIG. 14).

A significant feature of the experimental model of dog infection by sand fly bites was the appearance of skin lesions in various parts of the body (e.g. dog 3080, depicted in FIG. 15). These manifested as alopecia/dorsal neck lesions (A) or symmetrical (bi-lateral) paw lesions (B). Smears and/or positive cultures established the lesions were caused by Leishmania infantum. Another significant finding was the establishment that uninfected sand flies efficiently pick up the infection from skin lesions or the original site of transmission (FIG. 16A) but not from normal skin (FIG. 16B). This finding is of epidemiological importance since it begins to address the manner by which disease is disseminated between dogs in nature.

REFERENCES

MELBY et al., *J. Immunol.* 2001; 166; 1912-1920
LAWYER et al., *Transactions of the Royal Society of Tropical Medicine and Hygiene*. (1990) 84, 229-232.
PROBST et al., *Medical and Veterinary Entomology* (2001) 15, 12-21.
DONDJI et al., *Infection and Immunity*, August 2005, p. 5286-5289.
GRADONI & GRAMICCIA, *Parasitology Today*, vol. 10, no. 7, 1994\
WILSON et al., *Microbial Pathogenesis* 38 (2005) 147-160
KAMHAWI et al., *Science* 290, 1351 (2000)
PETERS et al., *PLOS Pathogens*. June 2009, Volume 5, Issue 6
ROGERS et al., *NATURE*, VOL 430, 22 JULY 2004
MORRIS et al., *J. Immunol.* 2001; 167; 5226-5230
TITUS & RIBEIRO, *SCIENCE*, VOL. 239, page 1306-8
GOMES et al., *PNAS*, Jun. 3, 2008_vol. 105_no. 22_7845-7850
KIMBLIN et al., *PNAS*, Jul. 22, 2008_vol. 105_no. 29_10125-10130

All references cited herein are incorporated herein, in their entirety, by reference.

The invention will now be described by the following non-limiting claims.

What is claimed is:

1. A method for infecting canine animals with a *Leishmania* parasite comprising the steps of:
   a. testing the canine animals to ensure they are free of *Leishmania* and not previously exposed to sand fly salivary proteins (naïve);
   b. transmitting the *Leishmania* parasite to the canines by means of *Leishmania*-infected sand fly bites; and
   c. quantifying the parasite load/fly and the % metacycles/fly (scoring the sand flies) post transmission to verify success of transmission, thereby infecting the canine animals.

2. The method of claim 1 further characterized in that the transmitting to the canines is performed using 10 to 50 bites of the infected sand flies.

3. The method of claim 1 or 2 wherein the infected sand flies harbor greater than or equal to 30,000 *Leishmania* parasites, and wherein greater than or equal to 50% of the parasites are metacycles.

4. The method of claim 3 further characterized in that the *Leishmania* parasite belongs to species *infantum*.

5. The method of claim 1 or 2 further characterized in that the testing of the canines includes testing for previous exposure to sand fly salivary peptides or proteins, or testing for the presence in the canine animals of *Leishmania*-specific components, including antigens, nucleic acids, proteins, peptides, or membrane components, or testing for the presence of host-produced components, including antibodies against said *Leishmania* components.

6. The method of claim 1 or 2 wherein the *Leishmania* parasite is a virulent strain isolated from a sick canine animal that is infected with the *Leishmania* parasite.

7. The method of claim 1 or 2 wherein the transmitting is done using multiple delivery or bite sites on the canine animals, to mimic what occurs under field conditions wherein canines are infected with *Leishmania* parasites via the biting action of *Leishmania*-infected sand flies.

8. The method of claim 1, which models naturally occurring *Leishmania* infection in canines, comprising the steps of:
   a. selecting canines six months or younger for infection;
   b. testing the canines for previous exposure to sand fly salivary proteins;
   c. infecting vector sand flies with a virulent isolate of *L. infantum* or other *Leishmania* spp., obtained from a canine infected with the *L. infantum* or other *Leishmania* spp., wherein only passages 5 or 4 or 3 or earlier of the *L. infantum* or other *Leishmania* spp. are used to carry out the infection, and wherein the infecting is accomplished by supplying the sand flies with blood containing *L. infantum* or other *Leishmania* spp.;
   d. monitoring the sand fly infection to follow the progression of the infection along the sand fly midgut;
   e. assessing the state of bacterial colonization in the sand fly;
   f. assessing an incremental increase in total parasite number with time and an incremental increase in appearance of metacyclics with time;
   g. scoring sand flies prior to every transmission event;
   h. using blood from *Leishmania*-infected canine(s) to infect groups of flies 1 or 2 or 3 times a week;
   i. carrying out on multiple sites over multiple transmissions of *Leishmania* spp. to dogs via sand fly bites; and
   j. scoring of sand flies used for transmission to assess feeding success and infection status, thereby infecting the canines, and modeling naturally occurring *Leishmania* infection in canines.

* * * * *